Figure 1:
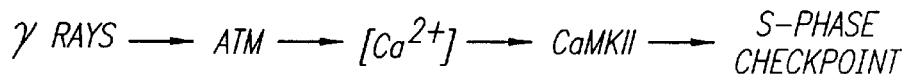
Figure 1:
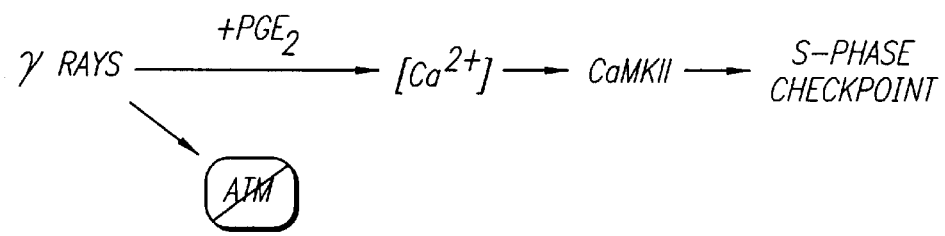

United States Patent [19]
Paterson et al.

[11] Patent Number: 5,990,168
[45] Date of Patent: Nov. 23, 1999

[54] METHODS AND COMPOSITIONS FOR THE TREATMENT OF ATAXIA TELANGIECTASIA

[75] Inventors: Malcolm C. Paterson, Riyadh, Saudi Arabia; Razmik Mirzayans, Edmonton, Canada

[73] Assignee: Alberta Cancer Board, Edmonton, Canada

[21] Appl. No.: 08/844,531

[22] Filed: Apr. 17, 1997

Related U.S. Application Data

[60] Provisional application No. 60/015,810, Apr. 18, 1996.

[51] Int. Cl.$^6$ .................................................. A61K 31/557
[52] U.S. Cl. ................................................ 514/573; 424/4
[58] Field of Search .................................. 514/573; 424/4

[56] References Cited

FOREIGN PATENT DOCUMENTS 2011969   3/1970   Germany .

OTHER PUBLICATIONS

Askew, et al., 1989, "Molecular Recognition with Convergent Functional Groups. Synthethic and Structural Studies with a Model Receptor for Nucleic Acid Components", *J. Am. Chem. Soc.* 111:108–1090.

Aurias and Dutrillaux, 1986, "A possible new type of chromosome rearrangement: telomere–centromere translocation (tct) followed by double duplication", Hum. Genet. 72: 25–26.

Aurias and Dutrillaux, 1986, "Probable involvement of immunoglobulin superfamily genes in most recurrent chromosomal rearrangements from ataxia telangiectasia", Hum. Genet. 72:210–214.

Bar et al., 1978, "Extreme Insulin Resistance in Ataxia Telangiectasia", New Eng. J. Med. 298:1164–1171.

Beamish and Lavin, 1994, "Radiosensitivity in ataxia–telangiectasia: anomalies in radiation–induced cell cycle delay", Int. J. Radiat. Biol. 65:175–184.

Bigbee et al., 1989, "Evidence for an Elevated Frequency of In Vivo Somatic Cell Mutations in Ataxia Telangiectasia", Am. J. Hum. Genet. 44:402–408.

Corey et al., 1969, Stereo–Controlled Synthesis of Prostaglandins $F_{2\alpha}$ and $E_2$ (dl), *J. Am. Chem. Soc.* 91:5675–5677.

Croce et al., 1985, "Gene for α–Chain of Human T–Cell Receptor: Location on Chromosome 14 Region Involved in T–Cell Neoplasms", Science 227:1044–1047.

Ford and Easton, 1995, "The genetics of breast of ovarian cancer", Br. J. Cancer 72:805–812.

Gatti et al., 1991, "Ataxia–Telangiectasia: An Interdisciplinary Approach to Pathogenesis", Medicine 70:99–117.

Hartwell and Kastan, 1994, "Cell Cycle Control and Cancer", Science 266:1821–1828.

Heather et al., 1973, "Total Synthesis of Prostaglandins. V. A Synthesis of (×)–Prostaglandin $E_2$ Via a Totally Asymmetric Process", Tetrahedron Letters 25:2313–2316.

Henderson et al., 1985, "Diagnosis of Ataxia–Telangiectasia by T–Lymphocyte Cloning Assay", Lancet 11:1242.

Hernandez et al., 1993, "A family showing no evidence of linkage between the ataxia telangiectasia gene and chromosome 11 q22–23", J. Med. Genet. 30:135–140.

Houghten et al., 1991, "Generation and use of synthetic peptide combinatorial libraries for basic research and drug discovery", Nature 354:84–86.

Hynes, 1992, "Integrins: Versatility, Modulation, and Signaling in Cell Adhesion", Cell 69:11–25.

Jaspers et al., 1988, "Genetic complementation analysis of ataxia telangiectasia and Nijmegen breakage syndrome: a survey of 50 patients", Cytogenet. Cell Genet. 49:259–263.

Kastan et al., 1992, "A Mammalian Cell Cycle Checkpoint Pathway Utilizing p53 and GADD45 Is Defective in Ataxia–Telangiectasia", Cell 71:587–597.

Kastan et al., 1991, "Participation of p53 Protein in the Cellular Response to DNA Damage", *Cancer Res.* 51:6304–6311.

Khanna & Lavin, 1993, "Ionizing radiation and UV induction of p53 protein by different pathways in ataxia–telangiectasia cells", Oncogene 8:3307–3312.

Kuerbitz et al., 1992, "Wild–type p53 is a cell cycle checkpoint determinant following irradiation", Pro. Natl. Acad. Sci. USA 89:7491–7495.

Kuhnlein and Paterson, 1990, "Increased uracil–DNA glycosylase, AP–DNA binding protein and deoxyribonuclease activities in tumor and SV40–transformed cell lines of huma origin", Carcinogenesis 11:117–121.

Lam, et al., 1991, "A new type of synthetic peptide library for identifying ligand–binding activity", Nature 354:82–84.

Lewis and Dean, 1989, "Automated site–directed drug design: the concept of spacer skeletons for primary structure generation", Proc. R. Soc. Lond. 236:125–140.

(List continued on next page.)

*Primary Examiner*—Robert Gerstl
*Attorney, Agent, or Firm*—Pennie & Edmonds LLP

[57] ABSTRACT

Embodiments of the invention include formulations for the treatment of (AT) ataxia telangiectasia patient and asymptomatic AT heterozygous carriers. The subject formulations comprise one or more different prostaglandins and a pharmaceutically acceptable carrier. Preferably the prostaglandins are group E prostaglandins, prostaglandin E2 being particularly preferred. Other embodiments of the invention include methods of treating AT patients and AT carriers. These methods comprise the steps of administering an effective amount of a prostaglandin containing composition of the invention. Other embodiments of the invention include methods of treating AT patients and carriers with radiotherapy. The methods comprise the steps of administering and effective amount of a prostaglandin containing formulations of the invention and subsequently irradiating the subject with an amount of radiation sufficient to achieve the desired therapeutic effect. Other embodiments of the invention include methods of radioimaging AT patients and AT carriers. The methods comprise the steps of administering an effective amount of a prostaglandin containing formulation of the invention and subsequently irradiating the subject with an amount of radiation to produce a diagnostic image of interest.

10 Claims, 2 Drawing Sheets

OTHER PUBLICATIONS

Lewis and Dean, 1989, "Automated site–directed drug design: the formation of molecular templates in primary structure generation", Proc. R. Soc. Lond. 236:141–162.

McKinaly and Rossmann, 1989, "Rational Design of Antiviral Agents", Annu. Rev. Pharmacol. Toxiciol. 29: 111–122.

Mohamed et al., 1987, "A Defect in DNA Topoisomerase II Activity in Ataxia–Telangiectasia Cells", Biochem. Biophys Res. Commun. 149:233–238.

Pippard et al., 1988, "Cancer in Homozygotes and Heterozygotes of Ataxia–Telangiectasia and Xeroderma Pigmentosum in Britain", Cancer Res. 48:2929–2932.

Ripka, Jun. 16, 1988, "Computers picture the perfect drug", New Scientist 54–57.

Rosin et al., 1989, "Heterogeneity of chromosomal breakage levels in epithelial tissue of ataxia–telangiectasia homozygotes and heterozygotes", Hum. Genet. 83:133–138.

Rouvinen et al., 1988, "Computer–Aided Drug Design", Acta Pharmaceutical Fennica 97:159–166.

Russo et al., 1989, "Molecular analysis of a t(14;14) translocation in leukemic T–cells of an ataxia telangiectasia patient", Proc. Natl. Acad. Sci. 86:602–606.

Savitsky et al., 1995, "A Single Ataxia Telangiectasia Gene with a Product Similar to PI–3 Kinase", Science 268:1749–1753.

Saxon et al., 1979, "Helper and Suppressor T–Lymphocyte Leukemia in Ataxia Telangiectasia", New Eng. J. Med. 300:700–704.

Sedgwick and Boder (1991) in *Handbook of Clinical Neurology: Hereditary Neuropathies and Spinocellular Atrophies* vol. 16(60) (P.J. Ninken et al., edu.), pp. 347–423, Elsevier Science, Amsterdam.

Shaham and Becker, 1981, "The Ataxia Telangiectasia Clastogenic Factor is a Low Molecular Weight Peptide", Hum. Genet. 58:422–424.

Shiloh et al., 1989, "$G_2$ chromosomal radiosensitivity in families with ataxia–telangiectasia", Hum. Genet. 84:15–18.

Songyang et al., 1993, "SH2 Domains Recognize Specific Phosphopeptide Sequences", Cell 72:767–778.

Swift et al., 1991, "Incidence of Cancer in 161 Families Affected by Ataxia–Telangiectasia", New Eng. J. Med. 325:1831–1836.

Swift et al., 1987, "Breast and Other Cancers in Families with Ataxia–Telangiectasia", New Eng. J. Med. 316:1289–1294.

Weeks et al., 1991, "Assessment of Chronic γ Radiosensitivity as an in Vitro Assay for Heterozygote Identification of Ataxia–Telangiectasia", Radiat. Res. 128:90–99.

Woods and Taylor, 1992, "Ataxia Telangiectasia in the British Isles: The Clinical and Laboratory Features of 70 Affected Individuals", Quart. J. Med. 82:169–179.

Wooster et al., 1993, "Absence of linkage to the ataxia telangiectasia locus in familial breast cancer", Hum. Genet. 92:91–94.

Zakian, 1995, "ATM–Related Genes: What do They Tell Us about Functions of the Human Gene?", Cell 82:685–687.

NORMAL CELLS

AT A CELLS

METHODS AND COMPOSITIONS FOR THE TREATMENT OF ATAXIA TELANGIECTASIA

RELATED APPLICATION

This Application claims priority to U.S. Provisional Application Serial No. 60/015,810, filed Apr. 18, 1996.

1.0. INTRODUCTION

The present invention relates to methods and compositions for treating ataxia telangiectasia in humans.

2.0. BACKGROUND

The normal eucaryotic cell cycle typically comprises four main stages. The replication of DNA and the production of histones occurs during the S phase. The period of DNA synthesis is flanked by two "gap" periods, the $G_1$ and $G_2$ phases, during which pre- and post-replication DNA repair may occur, and during which the cell continues to produce the cellular macromolecules required for cell division. After the $G_2$ phase, the cell will divide into two daughter cells during the M phase.

After irradiation, normal mammalian cells in S phase generally enter a period where DNA synthesis is arrested. The period of arrest provides a "checkpoint" in the cell cycle which allows time for the repair of DNA lesions, and thereby prevents replication of a faulty DNA template. Irradiation induced inhibition of DNA synthesis has been the subject of intensive research for many years (Hartwell and Kastan, 1994, Science 266:1821–1828). Recent results have reported a direct link between the ability of human cells to arrest in $G_1$ phase following irradiation, and the status of the p53 tumor suppressor gene (Kasten et al., 1991 *Cancer Res.* 51:6304–6311; Kuerbitz et al., 1992, *Pro. Natl. Acad. Sci. USA* 89:7491–7495). In brief, these studies linked irradiation with increased levels of p53 protein. Further studies have demonstrated that inhibitors of protein kinase C (PKC) may prevent enhanced p53 expression after irradiation (Khanna & Lavin, 1993 *Oncogene* 8:3307–3312). These data cumulatively suggest that both PKC and p53 may play a role in irradiation-induced arrest of $G_1$-S transition.

2.1. Ataxia Telangiectasia

Ataxia telangiectasia (AT) is an autosomal recessive, multi-system disorder characterized by progressive neuromuscular and vascular degeneration. AT is transmitted at an estimated frequency of one per 40,000 live births. AT patients exhibit cerebellar ataxia; oculocutaneous telangiectases; and various immune defects including underdevelopment of the thymus leading to recurrent sinopulmonary infections. Chromosomal breakage and rearrangement are common in AT cells which are abnormally sensitive to ionizing radiation. Moreover, both homozygous recessive AT patients and heterozygous carriers are predisposed to malignancy.

Onset of AT generally occurs by 3 years of age, and the first symptom is usually truncal ataxia (Woods, C. G. and Taylor, A. M. R. (1992) Quart. J. Med. 82:169–179). Truncal ataxia, which precedes appendicular ataxia, is characterized by deep tendon reflexes which become diminished or absent by age 8. Over time, patients lose large-fiber sensation. By their twenties and early thirties, many AT patients develop progressive spinal muscular atrophy which mostly affects the hands and feet. Familial studies revealed that idiopathic scoliosis and vertebral anomalies occurred in excess in the relatives of AT patients.

Ataxia was reviewed, inter alia, in *The Merck Manual of Diagnosis and Therapy*, 16th Ed. (1992) Merck Research Laboratories, Rahway, N.J. See also Sedgwick and Boder (1991) in *Handbook of Clinical Neurology: Hereditary Neuropathies and Spinocellular Atrophies* Vol. 16(60) (P. J. Ninken et al., edu.), pp. 347–423, Elsevier Science, Amsterdam.

2.2. AT-Associated Chromosomal Correlations

In the last five years it has become apparent that the basic defect underlying AT effects one or more of the enzymes concerned with DNA processing. Kuhnlein and Paterson (1990, Carcinogenesis 11:117–121) reported a 5–6 fold increase in activity for uracil DNA glycosylase and DNAse III/IV and a 2–3 fold increase in apurinic/apyrimidinic DNA-binding protein. A tight chromosomal linkage is found between AT and THY1, a glycoprotein which is a major cell surface constituent of thymocytes and neurons. In addition, genes of the immunoglobulin super family, including CD3 and NCAM, are located near the AT region of chromosome 11.

Aurias and Dutrillaux (1986a, Hum. Genet. 72:25–26; 1986b, Hum. Genet. 72:210–214) reported that AT patients tend to have a high frequency of chromosomal breakage, not involving the AT locus itself, which leads to both translocations and inversions. The sites of breakage and rearrangements mostly involve those regions of chromosomes 2, 7, 14, and 22 where the immunoglobulin genes (IgK, IgH, and IgL) and T-cell receptor genes (TCR-α, -β, and -γ) are located. Ig clusters are known hot spots for breakage and rearrangements and are associated with several diseases. Previously Croce et al. (1985, Science 227:1044–1047) had suggested that the oncogene TCL1 which is located in the region of the chromosome 14 breakpoint may be activated by chromosome inversion or translocation, perhaps in juxtaposition with the TCR-α gene. Russo et al. (1989, Proc. Natl. Acad. Sci. 86: 602–606) presented further evidence of a cluster of breakpoints in the region of the putative oncogene TCL1 in AT patients with chronic lymphocytic leukemia.

Shaham and Becker (1981, Hum. Genet. 58:422–424) identified an AT clastogenic (chromosome breaking) factor in the plasma of AT patients and in the culture medium of AT skin fibroblasts. This small peptide has a molecular weight in the range of 500 to 1000. Although clastogenic activity could not be demonstrated using cell extracts, cultured AT fibroblasts are reported to show spontaneous chromosomal recombination rates 30 to 200 times higher than found in cultured normal fibroblasts. Increased recombination, translocations and other chromosomal aberrations in lymphocytes, monocytes and fibroblasts undoubtedly contribute to increased cancer risk.

Abnormal V(D)J recombination, joining V segments of the TCR-γ with J segments of TCR-β occurs in peripheral blood lymphocytes of AT patients at a frequency 50- to 100-fold higher than normal. This frequency is roughly the same as the increase in the risk for lymphoid malignancy in these individuals. In addition, the J-α sequence has been implicated in some T-cell translocations which remove chromosomal material between q12 and q32 of chromosome 11 (Russo et al. (1989) Proc. Natl. Acad. Sci. 86: 602–606).

All of these examples strongly imply that the immunodeficiencies associated with AT are due to the physical loss or functional inactivation of genetic material. This hypothesis is further substantiated by the fact that AT homozygotes commonly display a 5- to 14-fold increase in the frequency of oral exfoliated cell micronuclei. In AT, this easily scorable cytogenetic abnormality can be used as a diagnostic tool to identify AT heterozygotes who commonly display an intermediate frequency of such micronuclei (Rosin et al., 1989 Hum. Genet. 83:133–138).

Bigbee et al. (1989, Am. J. Hum. Genet. 44:402–408) demonstrated an increased frequency of somatic cell mutation in vivo in individuals with AT. The authors speculated that the predisposition to somatic cell mutation may be related to the increased susceptibility to cancer in AT homozygotes. Heterozygotes for the disease did not appear to have a significantly increased frequency of such mutations.

2.3. AT-Associated Sensitivity To Radiation/Cell Cycle

Clearly AT cells are deranged in a signal transduction pathway that controls cell cycle arrest following DNA damage. The product of the gene responsible for AT operates upstream of the p53 protein, which plays a role in the $G_1$-S checkpoint that delays the cell cycle in cells with damaged DNA. In normal cells, p53 levels increase 3- to 5-fold by a post-translational mechanism after γ-irradiation; however, augmented p53 expression, and its subsequent induction of GADD45, does not occur in irradiated AT cells (Kastan et al. (1992) Cell 71:587–597). Another consistent feature of AT cells is that they do not temporarily arrest DNA synthesis in response to irradiation. In fact, radioresistant DNA synthesis is widely considered as the "molecular signature" of AT cells.

Checkpoints at both the $G_1$-S and the $G_2$-M transitions (Hartwell (1992) Cell 71:543–546) allow the cell to delay progress through the cell cycle. Checkpoints are thought to serve as surveillance mechanisms which detect DNA damage, and initiate the proper signal transduction pathways required to allow time for DNA repair processes to run their course before the cell proceeds to the next phase in the cell cycle.

Painter and Young (1982 Proc. Natl. Acad. Sci. 77:7315–7317) showed that the $G_1$-S checkpoint is inoperative in cells from AT patients. If the DNA is not repaired, abnormalities which could contribute to tumor development become permanent during the S phase. In fact, lymphoid, breast and other cancers are known to be increased in individuals heterozygous for germ line mutations of either p53 or the gene causing AT (Swift et al. 1991 New Eng. J. Med. 325:1831–1836; 1987, New Eng. J. Med. 316:1289–1294).

Shiloh et al. (1989, Hum. Genet. 84:15–18) presented evidence that the extent of chromatid damage induced in the $G_2$ phase of the cell cycle by a moderate dose of x-rays is markedly higher in AT cells than in normal controls. These data correlate with the inability of some AT cells to carry out DNA synthesis during the S phase of the cell cycle (Mohamed et al. (1987) Biochem. Biophys. Res. Commun. 149:233–238). Because patients with AT are unusually sensitive to x-rays, treatment of malignancy with conventional dosages of radiation can be fatal.

2.4. AT-Associated Biochemistry

AT patients usually show an increase in serum alpha-fetoprotein. This is consistent with immaturity of the liver and suggests that a functional ATM protein is required for normal tissue differentiation. Patients also show a decrease in immunoglobulins although different patients may show different immunoglobulin (Ig)-A, -E, and -G2 levels, ranging from normal to completely absent. DNA topoisomerase II, an enzyme that introduces transient double-strand breaks, are also expressed at abnormal levels in many, but not all, AT cell lines. These variations appear to be correlated with various chromosomal rearrangements as discussed above.

In contrast, the severity of sinopulmonary infections such as staphylococcal pneumonia, chronic bronchitis, etc. do not necessarily correlate with AT-associated immunodeficiency and may be related to other genetic factors.

Endocrine abnormalities such as gonadal dysgenesis or atrophy and an unusual form of diabetes mellitus in which glucose tolerance is markedly decreased have been reported. Experiments examining insulin resistance suggest the presence of antireceptor immunoglobulins in the plasma of AT patients (Bar et al. (1978) New Eng. J. Med. 298:1164–1171). Mental retardation is sometimes associated with AT, and some older patients may suffer a severe loss of short-term memory (Gatti et al. (1991) Medicine 70:99–117).

2.5. AT-Associated Malignancy

Patients with AT have a strong predisposition to malignancy, particularly lymphomas and chronic lymphatic leukemia. About one-third of patients develop malignancies during their shortened, less than 50 year, life-span. In general, lymphomas in AT patients tend to be of B-cell origin, and leukemias of the T-cell type. Neoplastic cells are often of thymic origin, and Saxon et al. (1979) New Eng. J. Med. 300:700–704) have suggested that malignant transformation of uncommitted T-lymphocyte precursors capable of differentiation contribute to the chronic lymphatic leukemia often reported for AT patients. Solid tumors, including medulloblastomas and gliomas, occur at elevated rates in AT patients (Gatti et al. (1991) Medicine 70:99–117).

Heterozygotes are also said to be predisposed to lymphomas, with a relative risk of developing cancer compared to the normal population of about 3.7 (Swift et al. (1991) New Eng. J. Med. 325:1831–1836). Using documented cancer incidence (rather than cancer mortality) in persons heterozygous for AT, relative risk of cancer of all types was 3.8 for men and 3.5 for women. The relative risk for breast cancer, the cancer most clearly associated with AT, in carrier women was 5.1. In two independent studies, 8 to 18 percent of patients with breast cancer were confirmed to be AT heterozygotes (Swift et al. (1987) New Eng. J. Med. 316:1289–1294; Pippard et al. (1988) Cancer Res. 48:2929–2932). More recently, the frequency of the ATM gene was estimated to be 0.005, which translates into 1% of the population being ATM heterozygous carriers. This, combined with a revised relative risk of approximately 3.9 for female carriers would result in about 4% of all breast cancers being attributable to the heterozygous presence of the defective form of the ATM gene. Ford and Easton, 1995, Br. J. Cancer 72:805–812. The ATM gene is located on 11q22-23. Wooster et al. (1993, Hum. Genet. 92:91–94) typed 5 DNA markers in this chromosomal region in 16 breast cancer families. They found no evidence for linkage between familial breast cancer and these markers and concluded that the contribution of AT to familial breast cancer is likely to be minimal.

2.6. Genetic Complementation

As early as 1977, Paterson et al. (*Research in Photobiology*. Plenum, New York) suggested the existence of 2 distinct types of ataxia telangiectasia. By 1988, Jaspers et al. (Cytogenet. Cell Genet. 49:259–263) had used genetic complementation studies on fibroblasts to identify six different genetic complementation groups. Four of these, called AB, C, D, and E are clinically indistinguishable, present no group-specific patterns of clinical characteristics or ethnic origin, and display frequencies among AT patients of approximately 55%, 28%, 14%, and 3%, respectively. Hernandez et al. (1993, J. Med. Genet. 30:135–140) cited evidence for the existence of these four complementation groups: AB, C, D, and E on chromosome 11q. The group D defect was corrected by transfer of genetic material from region 11q22-q23 into an AT affected fibroblast cell line and group E cells have a deoxyribophosphodiesterase deficiency. The existence of different complementation groups presumably reflects alterations in distinct intragenic functional domains, given that the disease is caused by a single gene (ATM).

2.7 Beta Integrins

The integrin family comprises 14 alpha subunits and 8 beta subunits (Hynes, 1992, Cell 69:11–25). A functional structure consists of one alpha and one beta subunit which partially extrudes from the cell. The receptor is a dimer which connects the cytoskeleton with the extracellular matrix proteins.

One of the primary roles of the integrins is cell adhesion. In their connection with the proteins of the extracellular matrix, integrins are in close proximity to growth factors and they act as anchors for individual cells such as platelets and lymphocytes. Internally, they interact with talin molecules of the cytoskeleton and provide a more stable structural framework for tissues such as the skin, organs such as the liver, and the arteries and veins of the vascular system.

In their transmembrane role, the alpha and beta integrins appear to be bidirectional signaling proteins. They are among a select few molecules that propagate messages from the inside of the cell to the outside. Signaling function is explained or modeled via conformational changes, specifically interaction between the alpha and beta subunits, associated with signal transduction. As signal receptors, these molecules regulate intracellular pH, intracellular free calcium, tyrosine phosphorylation of proteins, and inositol lipid turnover.

Slight alterations, even point mutations, can be correlated with the loss of signaling. Lack of appropriate integrin signaling may be associated with the failure to halt the cell cycle for repair of chromosomal damage following chemical or physical disruption (such as ionizing radiation) and result in the higher cancer incidence seen in AT patients and carriers.

Integrins play a role in the immune response through activation of lymphocytes and the maturation of B-cells. It also appears that integrins may be downregulated or absent in AT cells. The relative dearth of integrins could explain the structural and functional immaturity of the liver and some of the immune and metastatic complications which are often associated with AT. Finally, when the secretion of integrins is blocked, cells undergo apoptosis. This apoptosis could affect fetal development and result in the non-Mendelian ratios seen in the inheritance of AT. In particular, it appears that a deficiency of integrin beta subunit 1 characterizes the major genetic form of AT, namely complementation group A.

2.8. Present Methods Of AT-Diagnosis

Early-onset ataxia with telangiectasias permits diagnosis of AT. Before the appearance of telangiectases, clinical diagnosis is problematic because cerebellar ataxia and oculomotor apraxia are also typical of X-linked Pelizaeus-Merzbacher disease and Joubert's syndrome. Elevated levels of alpha-fetoprotein and carcinoembryonic antigen are the most useful clinical markers (Gatti et al. (1991) Medicine 70:99–117). Dysgammaglobulinemia, decreased cellular immune responses, and peripheral lymphopenia are supportive findings but they may or may not be expressed in all AT patients.

Henderson et al. (1985, Lancet 11:1242) devised a rapid diagnostic method based on the hypersensitivity of AT lymphocytes by gamma irradiation. Similar studies have employed fibroblasts or chorionic villus sampling. Shiloh et al. (1989, Hum. Genet. 84:15–18) used the extent of X-ray damage to chromatids in the G2 phase of AT heterozygous cells as a test of heterozygosity.

Painter and Young (1980, Proc. Natl. Acad. Sci. 77:7315–7317), however, questioned the reliability of this approach on the basis that radiosensitivity of AT cells may be caused by their failure to delay DNA synthesis after radiation damage (see sensitivity to radiation/cell cycle above).

The exfoliated cell micronucleus test is performed on cells from either the oral cavity collected by swabbing the mucosa or the urinary bladder obtained by centrifugation of fresh urine specimens. Micronuclei are membrane-bound, Feulgen-positive, acentric fragments which result from fragmentation of chromosomes during division of epithelial cells. Both AT homozygotes and heterozygotes can be identified by this method (Rosin and Ochs 1986, Hum. Genet. 74:335–340, 1989 Hum. Genet. 83:133–138).

2.9. Identification of the Gene for AT

A breakthrough in the study of AT occurred recently with the identification of the gene underlying AT (Savitsky et al., 1995, Science 268:1749–1753). This gene, denoted ATM (ataxia-telangiectasia mutated), encodes a putative transcript of 12 kb specifying a protein homologous to the cytoplasmic signal transducer phosphatidylinositol 3-kinase (PI3K). Recent studies on ATM-related genes containing PI3K motifs have uncovered a family of genes, namely, *S. cerevisiae* TOR1, TOR2, TEL1 and *S. pombe* rad3, Drosophila mei-41, and the human gene encoding DNA-damage protein kinase catalytic subunit (DNA-PK$_{cs}$) (Zakian, 1995, Cell 82:685–687), which are more similar to one another than to classical PI3K. Notably, the cellular phenotype conferred by these ATM-like genes suggest their products have partially overlapping functions in mediating various cell-cycle checkpoints. This is perhaps not surprising, given that, as noted earlier, the extent of cell cycle deregulation is widespread in AT cells after radiation exposure (Beamish and Lavin, 1994, Int. J. Radiat. Biol. 65:175–184).

3.0. SUMMARY OF THE INVENTION

Ataxia telangiectasia (AT) is a serious genetic disease that produces several different clinical abnormalities. Among those abnormalities is increased sensitivity to ionizing radiation and chemically generated free radicals. This increased sensitivity is found both in ataxia telangiectasia patients and heterozygous carriers of the syndrome (Weeks et al., 1991, Radiat. Res. 128:90–99). Embodiments of the invention include methods and compositions for the treatment of clinical symptoms in both AT patients and AT carriers.

Embodiments of the invention include formulations for the treatment of AT and AT carriers. The subject formulation comprise one or more different prostaglandins and a pharmaceutically acceptable carrier. Preferably the prostaglandins are group E prostaglandins, prostaglandin E2 being particularly preferred.

Accordingly, a preferred embodiment of the present invention is the use of prostaglandins, particularly group E prostaglandins, and more particularly prostaglandin E2, in the preparation of a medication for treating ataxia telangiectasia. The medication may also be used for the preventative or palliative treatment of ataxia telangiectasia (heterozygous) carriers.

Other embodiments of the invention include methods of treating AT patients and AT carriers. These methods comprise the steps of administering an effective amount of a prostaglandin containing composition of the invention.

Other embodiments of the invention include methods of treating AT patients and carriers with radiotherapy. The methods comprising the steps of administering and effective amount of a prostaglandin containing formulations of the invention and subsequently irradiating the subject with an amount of radiation sufficient to achieve the desired therapeutic effect.

Other embodiments of the invention include methods of radioimaging AT patients and AT carriers. The methods comprise the steps of administering an effective amount of a prostaglandin containing formulation of the invention and subsequently irradiating the subject with an amount of radiation to produce a diagnostic image of interest.

4.0. BRIEF DESCRIPTION OF THE FIGURES

FIG. 1 represents a model pathway by which normal (non AT) cells suspend DNA synthesis after exposure to ionizing radiation. In brief, after exposure to gamma or other ionizing radiation, the ATM product is involved in a calcium dependant regulatory cascade that activates CaM kinase II. CaMKII in turn triggers the S-phase checkpoint (temporary inhibition of DNA synthesis). In AT A cells, the ATM gene product is defective and the S-phase checkpoint is not activated (i.e., radioresistant DNA synthesis proceeds). The exogenous addition of the eicosanoid $PGE_2$ (Prostaglandin $E_2$), or possibly other prostaglandins or derivative thereof, shunts the ATM defect and corrects the S-phase checkpoint defect in irradiated AT A cells.

Figure 2:
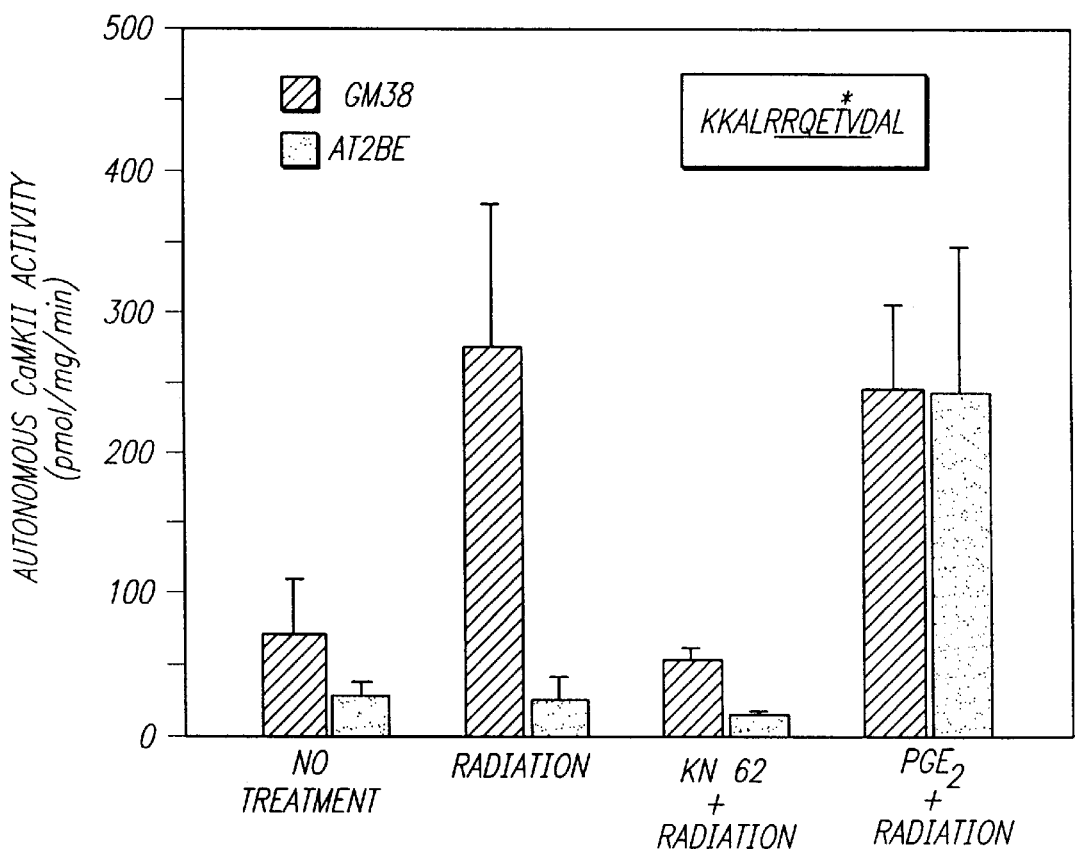

FIG. 2 compares the induction of autonomous CaMKII (calmodulin-dependent kinase II) activity of normal (GM38) and AT (AT2BE) fibroblasts after γ irradiation. The CaMKII activity is also compared in the presence or absence of $PGE_2$ or a selective antagonist of CaMKII (KN 62). CaMKII activity was measured using autocamtide 2 as an in vitro substrate. The core autophosphorylation sequence is underlined, and the phosphorylation target (threonine) is indicated by a asterisk.

Figure 3:
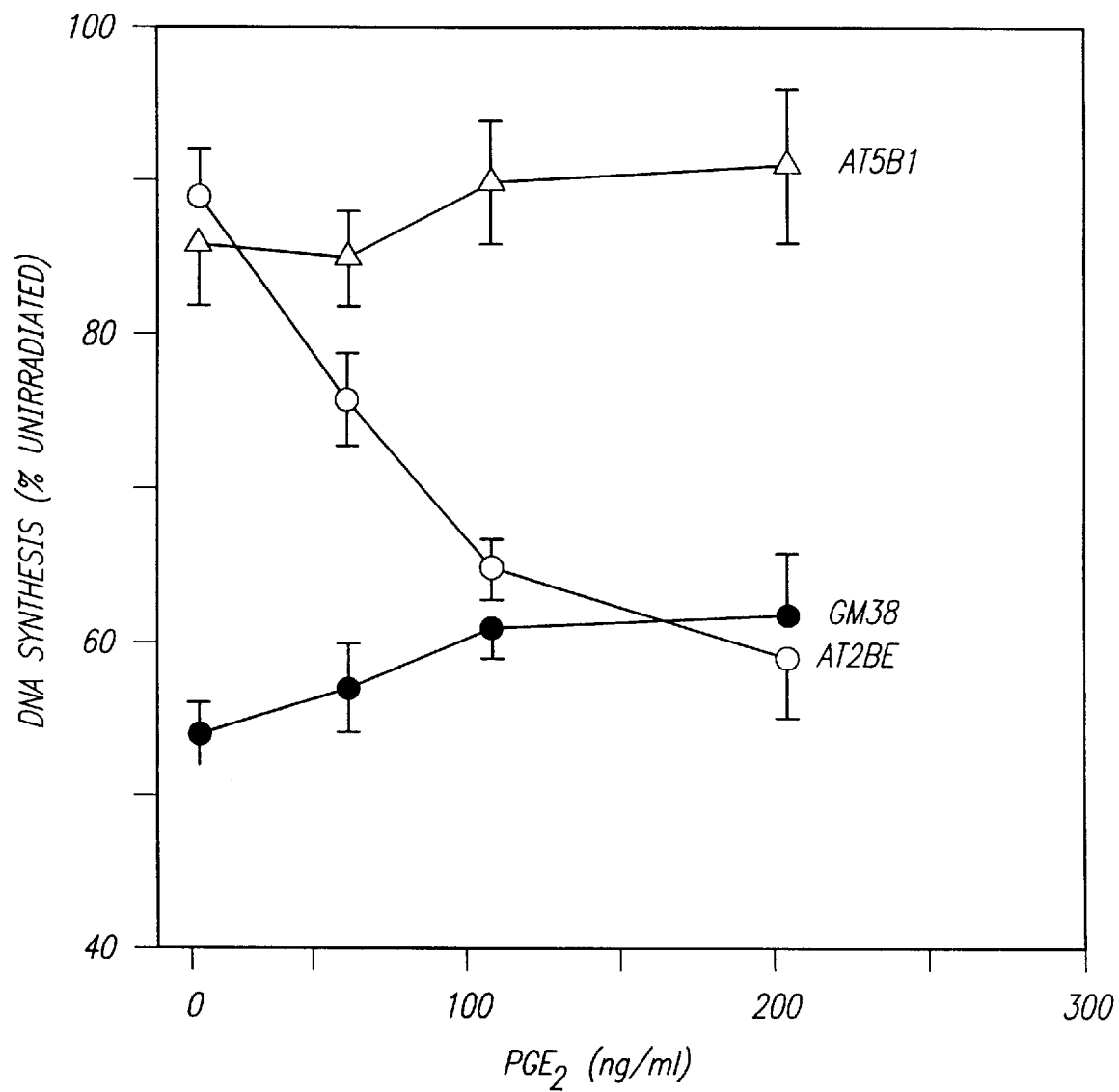

FIG. 3 shows the effect of $PGE_2$ on DNA synthesis inhibition induced by γ irradiation of normal (GM38), and AT group A (AT2BE), and AT group D (AT5BI) fibroblasts. The rate of DNA synthesis in irradiated cultures is expressed as a percentage of unirradiated controls. The addition of $PGE_2$ clearly corrects the levels of radioresistant DNA synthesis in AT A cells.

5.0. DESCRIPTION OF THE INVENTION

The invention provides methods and compositions for the treatment of ataxia telangiectasia and related conditions in ataxia telangiectasia heterozygous carriers. The invention relates, in part, to the inventors' surprising discovery that exogenously added prostaglandin may be used to correct the failure of AT A cells to undergo S-phase delay in response to irradiation and thereby acts as an extracellular signal modulator of the DNA damage surveillance network. The inventors' discovery, when viewed in conjunction with data provided in co-pending U.S. patent application Ser. No. 08/407,883, filed Aug. 28, 1995, which is herein incorporated by reference, suggests a model for the relationship between prostaglandin synthesis and ataxia telangiectasia. A diagram of this model is generally provided in FIG. 1. This model relates prostaglandin synthesis to a calcium/calmodulin-dependent pathway that mediates radiation-induced inhibition of DNA synthesis. This mechanism is disturbed in cells of AT patients and may possibly be disturbed, to a less extent, in the cells of AT carriers. In the model, endogenously produced prostaglandin binds to a prostaglandin receptor. The bound prostaglandin receptor activates the calmodulin mediated repression of DNA synthesis (at the S-phase checkpoint) in cells that have been exposed to DNA damaging agents or ionizing radiation. This calmodulin mediated repression is normally activated by ATM (the protein encoded by the ataxia telangiectasia mutated gene).

The model described above and displayed in FIG. 1 is provided solely for descriptive purposes, and is not intended as an express limitation of the invention. The invention as provided herein is operable irrespective of the accuracy of the model.

The discovery that prostaglandins can be used to restore a normal radiation-triggered DNA synthesis inhibition in AT cells has clinical significance. Prostaglandins may be used to treat some of the adverse symptoms associated with both AT and the AT carrier state. Of particular significance is the sensitivity of AT sufferers and AT carriers to ionizing radiation exposure and chemically generated free radicals. Ionizing radiation exposure of concern to AT sufferers and AT carriers frequently occurs during radiotherapy for cancer and during diagnostic radioimaging, e.g., x-rays, CAT scans, etc. Furthermore, in addition to radiation sensitivity, the prostaglandins containing formulations of the invention may be used to treat symptoms associated with AT and the AT carrier state.

The invention provides pharmaceutical formulations for use in the treatment methods described herein. The formulations comprise at least one prostaglandin and a pharmaceutically acceptable carrier. Preferably, the formulations comprise a group E prostaglandin, more preferably prostaglandin $E_2$. The structure and synthesis of many prostaglandins, both naturally occurring and synthetic derivatives thereof, are well known to the person of ordinary skill in the art. A detailed description of the structure, function, isolation, and synthesis of prostaglandins can be found, among other places in: *The Prostaglandins* Vols. 1, 2, P. Ramwell, Ed. (Plenum Press, N.Y., 1973, 1974), *Methods Enzymology, Vol. 86, Prostaglandins and Arachidonate Metabolites,* W. E. Landis, W. L. Smith Eds. (Academic Press, N.Y. 1982), J. S. Biadra, *Prostaglandin Synthesis* (Academic Press, N.Y. 1977). Additionally, the synthesis of prostaglandin $E_2$, can be found in German Patent No. 2,011,969 (1970), Heather et al., *Tetrahedron Letters* 1973, 2313, Corey et al. *J. Am. Chem. Soc.* 91, 5675, (1969), and the like. The formulations may comprise several prostaglandins. Specific prostaglandins for use in the subject methods and formulations may be selected by virtue of their ability to induce DNA synthesis inhibition in irradiated AT cells using assays described in the examples section below and in U.S. patent application Ser. No. 08/407,883. The ratio of the prostaglandins components of the subject formulation may vary over a wide range. Instead of prostaglandins, or in addition to prostaglandins, the subject formulations may comprise prostaglandin analogues that are agonists for prostaglandin receptors that are bound by prostaglandins that have a therapeutic effect on AT patients or AT carriers.

Such analogues may include, but are not limited to, peptides such as, for example, soluble peptides, including but not limited to members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L-configuration amino acids, phosphopeptides (including, but not limited to members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Computer modelling and searching technologies permit identification of compounds, or the improvement of already identified compounds, that can interact with the prostaglandin receptor. Having identified such a compound or composition, the active (e.g., binding sites) sites or regions are identified. Such active sites might typically be ligand binding sites, such as the regions where prostaglandins bind their cognate receptors. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. The compounds found from this search are potential prostaglandin analogues.

Alternatively, the above methods may be used to identify improved analogues of an already known compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified analogues or ligands of improved specificity or activity.

Further experimental and computer modeling methods useful to identify modulating compounds based upon identification of the prostaglandin receptor active sites, and related transduction and transcription factors, will be apparent to those of skill in the art.

Examples of molecular modelling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen, et al., 1988, *Acta Pharmaceutical Fennica* 97:159–166; Ripka, *New Scientist* 54–57 (Jun. 16, 1988); McKinaly and Rossmann, 1989, *Annu. Rev. Pharmacol. Toxiciol.* 29:111–122; Perry and Davies, *OSAR: Quantitative Structure-Activity Relationships in Drug Design* pp. 189–193 (Alan R. Liss, Inc. 1989); Lewis and Dean, 1989 *Proc. R. Soc. Lond.* 236:125–140 and 141–162; and, with respect to a model receptor for nucleic acid components, Askew, et al., 1989, *J. Am. Chem. Soc.* 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

The subject formulations may further comprise a variety of pharmaceutically acceptable carriers. A variety of aqueous carriers may be used, e.g. water, buffered water, 0.4% saline, 0.3% glycine, and the like. As prostaglandins are substantially hydrophobic, preferred carriers are hydrophobic or comprise pharmaceutically acceptable emulsifying agents, such as ethylene glycol distearate, Triton X-15, methylcellulose, gelatin, tragacanth, and the like. The subject formulations may also be in the form of liposomes. The pharmaceutical formulations may also comprise additional components that serve to extend the shelf-life of the pharmaceutical formulation. Such compounds include preservatives and the like. The formulations are preferably sterile and free of particulate matter (for injectable forms). These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The formulations of the invention may be adapted for various forms of administration, including intramuscularly, subcutaneously, intravenously, topically, by inhalation, intranasally, and the like. The subject formulations may also be formulated in a solid or semisolid form so as to provide for the sustained release of the prostaglandins. Examples of such sustained release formulations include composites of biocompatible polymers such as poly (lactic acid), poly (lactic-co-glycolic acid), methylcellulose, hyaluronic acid, collagen, and the like.

To produce pharmaceutical preparations in this form of dosage units for oral application containing a compound of the invention, the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax® or other polyethylene glycol waxes and are compressed to form tablets or cores for dragees. If dragees are required, the cores may be coated, for example, with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the preparation of soft gelatine capsules consisting of gelatine and, for example, glycerol as a plasticizer, or similar closed capsules, the active substance may be admixed with a Carbowax® or a suitable oil as e.g. sesame oil, olive oil, or arachis oil. Hard gelatine capsules may contain granulates of the active substance with solid, pulverulent carriers such as lactose, saccharose, sorbitol, mannitol, starches (for example) potato starch, corn starch or amylopectin), cellulose derivatives or gelatine, and may also include magnesium stearate or stearic acid as lubricants.

Actual methods for preparing administrable pharmaceutical formulations and adjustments necessary for administration to subjects will be known or apparent to those skilled in the art and are described in more detail in, for example, Remington's *Pharmaceutical Science*, 15th Ed., Mack Publishing Company, Easton Pa. (1980) and *Pharmaceutical Dosage Forms and Drug Delivery Systems*, Sixth edition, by Ancel et al., Williams & Wilkins, Baltimore (1995), which are incorporated herein by reference.

Some of the embodiments of the invention are methods for treating ataxia telangiectasia sufferers and ataxia telangiectasia carriers. The terms "treatment" or "treating" as used herein with reference to ataxia telangiectasia (or the carrier state) refer both to prophylaxis and to the amelioration of symptoms already present in an individual. It will be appreciated by the person of ordinary skill in the art that a treatment need not be completely effective in preventing the onset of a disease or in reducing the symptoms associated with the disease. Any reduction of the severity of symptoms, delay in the onset of symptoms, or delay in the progression of severity of symptoms is desirable to a patient. Persons at risk of developing symptoms may be treated prophylactically based on any of a variety of factors suggesting the possible onset of the disease, e.g., family history, genetic markers, early symptoms, and the like.

One embodiment of the methods of the invention comprises the step of administering an effective amount of a subject pharmaceutical formation comprising one of more prostaglandins (as described above). An "effective amount" is a dose of sufficient size to have a detectable therapeutic effect. For the purposes of the present disclosure, the term "therapeutic" shall refer to any treatment that enhances a patient's prognosis, or otherwise hinders, forestalls, or substantially prevents the adverse consequences of a disease or treatment in any way whatsoever. Similarly, the term "reducing the adverse effects" shall refer to a given method or formulation's ability to provide a therapeutic benefit to a patient by substantially ameliorating side-effects or medical treatments or procedures.

Preferred prostaglandins for use in the claimed methods belong the E group of prostaglandins. Prostaglandin $E_2$ is particularly preferred for use in the subject methods. The compositions administered in the subject methods may be administered systemically or locally.

Other embodiments of the invention include methods of reducing the adverse effects of radiation therapy (typically for cancer treatment) and the adverse effects of radiation exposure that results from diagnostic radioimaging, e.g., X-rays, CAT scans, and the like. In particular, the subject methods and formulations are deemed to be useful for reducing the adverse effects of routine preventative radioimaging procedures such as dental x-rays, chest x-rays, mammography, and the like. Such methods comprise the step of administering an effective amount of a subject pharmaceutical formation comprising one or more prostaglandins (as described above). The subject methods of radioimaging and radiotherapy further comprise the step of irradiating the subject either before or after the prostaglandin containing formulation is administered. In the case of radioimaging, the amount of irradiation employed will vary with the particular diagnostic method, but will be sufficient to produce a diagnostic image. Similarly, in the case of radiotherapy, the amount of irradiation employed will vary with the particular therapeutic method, but will be sufficient to produce the desired therapeutic effect.

An effective dosage and treatment protocol may be determined by conventional means, starting with a low dose in laboratory animals and tissue culture, then increasing the dosage while monitoring the effects, and systematically varying the dosage regimen as well. Numerous factors may be taken into consideration by a clinician when determining an optimal dosage for a given subject. These factors include the size of the patient, the age of the patient, the general condition of the patient, the severity of the disease, the presence of other drugs in the patient, and the like. The trial dosages would be chosen after consideration of the clinical literature with respect to administration of the specific prostaglandins selected. The terms "dosage" and "dose" as used herein, unless indicated otherwise, may refer not only to a single administration of a composition but may be used to refer to the total amount of a given pharmaceutical composition administered over a selected period of time and involving multiple individual administration.

The invention may be better understood in view of the following experiments. These experiments are offered to illustrate the invention and should not be construed as limiting the invention in any way whatsoever.

6.0. EXPERIMENTS

Two series of experiments were performed. In the first series of experiments, the induction of autonomous calmodulin-dependent kinase II (CaMKII) activity by γ radiation in normal and AT cells was determined; the effects of KN 62 (an antagonist of CaMKII) or $PGE_2$ (prostaglandin $E_2$) on this induction process were also determined. In the second series of experiments, the effects of $PGE_2$ on DNA synthesis inhibition induced by γ rays in normal and AT cells were measured.

6.1. Methods 6.1.1. Induction of CaMKII Activity by γ rays

Log phase normal (strains GM38) and AT (strain AT2BE) fibroblast cultures were held in serum-free medium for 90 min, incubated with KN 62 (10 μM) or prostaglandin $E_2$ (PGE$_2$) (200 ng/ml) for 30 min and irradiated (10 Gy). Cultures were lysed immediately and cell-free soluble extracts were assayed for CaMKII activity, both $Ca^{2+}$-independent (minus $Ca^{2+}$, unstimulatory or autonomous activity) and $Ca^{2+}$-dependent (plus $Ca^{2+}$, stimulatory activity), using the peptide autocamtide 2 as the in vitro substrate (Hanson et al., *Neuron* 3:59, 1989).

6.1.2. Effect of Exogenous PGE$_2$ on Post-γ ray DNA Synthesis

Normal and AT cultures were incubated with different concentrations of PGE$_2$ for 30 min and γ irradiated (10 Gy); control cultures were incubated with PGE$_2$ and sham-irradiated. All cultures were then incubated (37° C.) in the same PGE$_2$-containing medium for 15 min, and for an additional 45 min in fresh PGE$_2$-containing medium [$^3$H]-thymidine was added during the last 30 min and the amount of radioactivity incorporated into cellular DNA determined.

6.2. Results

As indicated in FIG. 2, the radiation treatment served to autophosphorylate CaMKII in normal cells such that autonomous ($Ca^{2+}$-independent) CaMKII activity was increased four-fold relative to the basal (unphosphorylated) level of activity. In contrast, autonomous CaMKII activity was not elevated in cell homogenates from γ ray-damaged AT cultures, nor was it raised in cell extracts from normal cultures which had been treated with KN 62 prior to radiation exposure.

Parallel experiments on $Ca^{2+}$-dependent CaMKII activity indicated that both normal and AT cells contain similar amounts of stimulatory activity (~1000-fold above basal level) which were unaffected by radiation or PGE$_2$ treatment (data not shown); hence AT cells contain normal levels of CaMKII protein but are unable to trigger the induction of the autonomous activity on sustaining radiation damage. Interestingly, addition of PGE$_2$ to the culture medium of AT complementation group A cells fully corrected the defect in γ ray-induced expression of autonomous CaMKII activity (FIG. 2). Treatment with PGE$_2$ also enabled AT A cells (but not AT D cells), when faced with radiation injury, to shut down the DNA synthesis machinery to an extent comparable to that achieved by normal cells (FIG. 3).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. A method for treating ataxia telangiectasia in a mammal, said method comprising the step of administering an effective amount of one or more prostaglandins to a mammal in need of said treatment, wherein said one or more prostaglandins are effective for treating ataxia telangiectasia.

2. A method according to claim 1 wherein at least one of said prostaglandins is a prostaglandin E.

3. A method according to claim 2, wherein said prostaglandin E is prostaglandin $E_2$.

4. An improved method of treating an ataxia telangiectasia patient or ataxia telangiectasia carrier with radiotherapy, said method comprising the steps administering an effective amount of one or more prostaglandins to said patient; and irradiating said patient with a therapeutic level of radiation, wherein said one or more prostaglandins are effective for treating ataxia telangiectasia.

5. A method according to claim 4 wherein at least one of said prostaglandins is a prostaglandin E.

6. A method according to claim 5, wherein said prostaglandin E is prostaglandin $E_2$.

7. An improved method of radioimaging an ataxia telangiectasia patient or ataxia telangiectasia carrier, said method comprising the steps administering an effective amount of one or more prostaglandins to said patient; and irradiating said patient with a level of radiation sufficient to produce a diagnostic image, wherein said one or more prostaglandins are effective for treating ataxia telangiectasia.

8. A method according to claim 7 wherein at least one of said prostaglandins is a prostaglandin E.

9. A method according to claim 8, wherein said prostaglandin E is prostaglandin $E_2$.

10. The method according to claim 1, wherein the mammal is a human.

* * * * *